(12) United States Patent
Kronemayer et al.

(10) Patent No.: US 8,455,676 B2
(45) Date of Patent: Jun. 4, 2013

(54) PROCESS FOR PREPARING CARBOXYLIC ESTERS BY REACTIVE DISTILLATION

(75) Inventors: Helmut Kronemayer, Heidelberg (DE); Ellen Dahlhoff, Limburgerhof (DE); Andreas Lanver, Mannheim (DE)

(73) Assignee: BASF SE, Ludwigshafen (DE)

( * ) Notice: Subject to any disclaimer, the term of this patent is extended or adjusted under 35 U.S.C. 154(b) by 64 days.

(21) Appl. No.: 13/088,822

(22) Filed: Apr. 18, 2011

(65) Prior Publication Data

US 2011/0257426 A1 Oct. 20, 2011

Related U.S. Application Data

(60) Provisional application No. 61/325,432, filed on Apr. 19, 2010.

(51) Int. Cl.
*C07C 67/02* (2006.01)

(52) U.S. Cl.
USPC .......................................................... 560/234

(58) Field of Classification Search
CPC .................................................... C07C 67/03
See application file for complete search history.

(56) References Cited

U.S. PATENT DOCUMENTS 1,433,308 A * 10/1922 Steffens ........................ 560/234
5,302,747 A    4/1994 Nelson et al.

FOREIGN PATENT DOCUMENTS

| DE | 10 2007 006 917 A1 | 8/2008 |
|---|---|---|
| EP | 0 968 995 B1 | 1/2000 |
| JP | 10-175916 | 6/1998 |
| WO | WO 2007/099071 A1 | 9/2007 |

OTHER PUBLICATIONS

U.S. Appl. No. 13/087,844, filed Apr. 15, 2011, Kronemayer, et al.
U.S. Appl. No. 12/740,468, filed Apr. 29, 2010, Windecker, et al.
U.S. Appl. No. 13/024,786, filed Feb. 10, 2011, Lanver, et al.
Liu et al., Transesterification of Methanol with Ethyl Aceteat eand Ethanol and Methyl Formate Catalyzed by DBN, Journal of Natural Gas Chemistry, vol. 7, No. 4, 1998.
International Search Report issued in corresponding application No. PCT/EP2011/056189 dated Oct. 24, 2011.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

In a process for preparing carboxylic esters by transesterification, a first feed stream comprising a first carboxylic ester, e.g. methyl formate, is introduced laterally into a reaction column at least one first feed point located between top and bottom of the reaction column and a second feed stream comprising a first alcohol, e.g. ethanol, is introduced laterally into the reaction column at a second feed point located above the first feed point and are reacted in a reaction zone of the reaction column to form a second carboxylic ester and a second alcohol. The first alcohol has a higher molecular weight than the second alcohol. A product fraction comprising the second carboxylic ester and unreacted first carboxylic ester is taken off at an offtake point located above the second feed point. At the bottom of the reaction column, a bottom fraction comprising the second alcohol and unreacted first alcohol is taken off. The product fraction is separated by distillation at a pressure which is different from the pressure in the reaction column into second carboxylic ester and a fraction comprising unreacted first carboxylic ester and the fraction comprising unreacted first carboxylic ester is at least partly recirculated to the reaction zone.

16 Claims, 1 Drawing Sheet

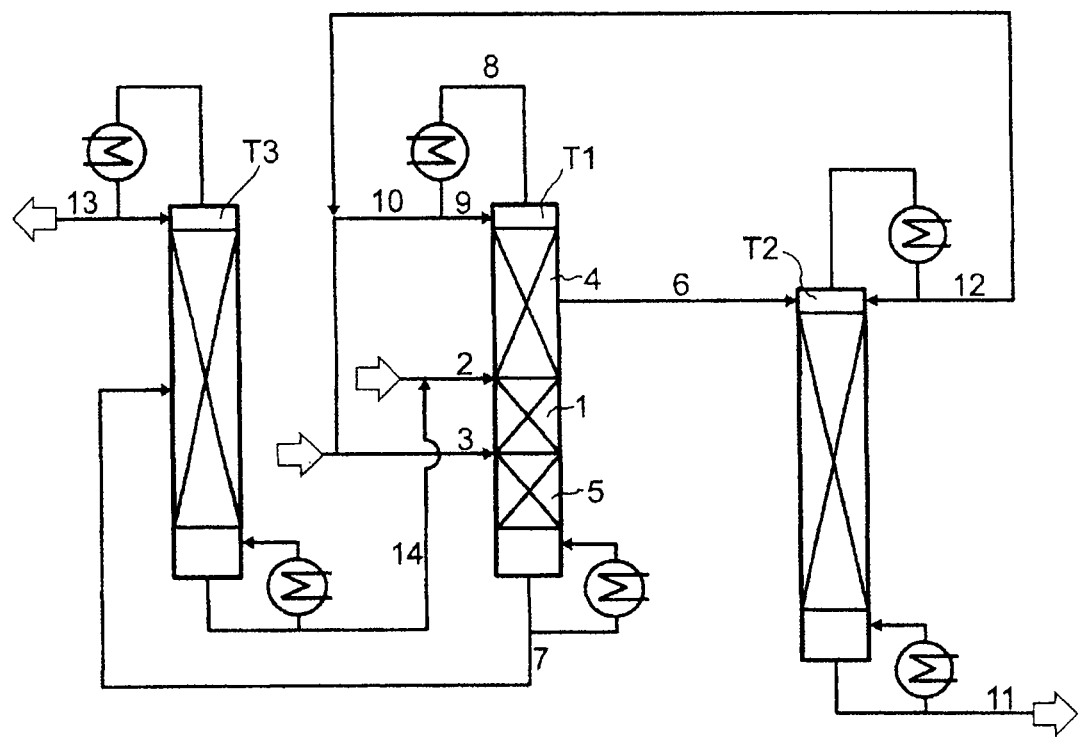

PROCESS FOR PREPARING CARBOXYLIC ESTERS BY REACTIVE DISTILLATION

CROSS-REFERENCE TO RELATED APPLICATIONS

This application claims the benefit of priority under Section 119(e) to U.S. Provisional Application No. 61/325,432 filed on Apr. 19, 2010.

BACKGROUND OF THE INVENTION

The invention relates to a process for preparing carboxylic esters, in particular ethyl formate, by transesterification.

Low molecular weight esters such as formic esters are employed, for example, as fragrances, insecticides, fungicides or in organic synthesis. Processes for preparing low molecular weight esters have been widely described in the literature. An inexpensive possibility is esterification of carboxylic acid and alcohol with subsequent distillation of the ester. In many cases, this process can be carried out very simply in industry because the product in the form of the ester is the lowest-boiling compound.

U.S. Pat. No. 5,302,747 describes a process in which an inert gas is passed through an esterification mixture which comprises an alcohol and a carboxylic acid and is maintained at at least the boiling point of the alcohol in order to drive off the ester.

The preparation of highly pure esters, in particular formic esters, having a purity of greater than 99.5% by weight, in particular greater than 99.8% by weight, is difficult, as will be explained below for the example of the esterification of formic acid with ethanol. The esterification of formic acid with ethanol forms water and ethyl formate. In the distillation of the reaction product, it is possible to separate neither ethanol nor water completely from the ester since both materials form azeotropes with the ester over wide pressure ranges. As a result, highly pure ethyl formate cannot be obtained by this route.

JP 10175916 describes the preparation of highly pure formic esters. The esterification of formic acid and alcohol is carried out by reactive distillation, with the distillate obtained being dewatered by means of acetic anhydride. Although water can be removed by use of desiccants in this process, unreacted alcohol cannot be removed in a comparable way.

WO 2007/099071 describes the preparation of esters by reactive distillation. A carboxylic acid, an alcohol and an entrainer are introduced into a reaction column. The bottom stream comprises the ester formed and unreacted carboxylic acid. The overhead stream comprises unreacted alcohol, water and entrainer.

The preparation of an ester from the carboxylic acid and alcohol has the disadvantage that the acid is generally corrosive and acid-resistant materials have to be used for handling it.

BRIEF SUMMARY OF THE INVENTION

It is an object of the invention to provide a process for preparing highly pure esters which is economical to carry out and envisages relatively low capital costs for apparatuses and in particular overcomes the requirement of acid-resistant materials.

This object is achieved according to the invention by a process for preparing carboxylic esters by transesterification, wherein a first feed stream comprising a first carboxylic ester and a second feed stream comprising a first alcohol are introduced into a reaction column and reacted in a reaction zone of the reaction column to form a second carboxylic ester and a second alcohol, where the first alcohol has a higher molecular weight than the second alcohol and the second carboxylic ester and the second alcohol are continually removed from the reaction zone.

The process is suitable for preparing low molecular weight carboxylic esters which can be vaporized without decomposition. A first carboxylic ester which is the ester of a carboxylic acid with the second alcohol is used as starting material. The first carboxylic ester is preferably an ester of a $C_1$-$C_5$-carboxylic ester, e.g. an ester of formic acid, acetic acid, propionic acid, chloroacetic acid, bromoacetic acid, lactic acid, glycolic acid. In particular, the first carboxylic ester is a formic ester.

The first alcohol has a higher molecular weight than the second alcohol. In appropriate embodiments, the first alcohol is a $C_2$-$C_5$-alcohol, preferably ethanol, and the second alcohol is methanol.

A particularly preferred embodiment provides a process for preparing ethyl formate, wherein the first carboxylic ester is methyl formate and the first alcohol is ethanol.

BRIEF DESCRIPTION OF THE DRAWING

FIG. 1 schematically shows one embodiment of a plant suitable for carrying out the process of the invention.

DETAILED DESCRIPTION OF THE INVENTION

For the purposes of the present invention, a "reaction zone" is a region of the reaction column in which suitable conditions, in particular in respect of temperature, pressure and presence of a catalyst, prevail, so that the reaction between the first carboxylic ester and the first alcohol proceeds at an appropriate rate. Mass transfer takes place in the reaction zone in parallel with the chemical reaction. The removal of the second carboxylic ester and the second alcohol from the reaction zone firstly shifts the reaction equilibrium and secondly prevents subsequent reactions, resulting in a large increase in the selectivity of the reaction.

The reaction column comprises separation-active internals such as separation trays, e.g. perforated trays, valve trays or trays characterized by a long residence time, ordered packings, e.g. sheet metal or woven mesh packings such as Sulzer Mellapak 250Y, Sulzer BX, Montz B1 or Montz A3 or Kühni Rhombopak, or random beds of packing elements, e.g. Dixon rings, Raschig rings, High-Flow rings or Raschig Super Rings. Ordered packings, preferably sheet metal or woven mesh packings, having a specific surface area of from 100 to 750 $m^2/m^3$, in particular from 250 to 500 $m^2/m^3$, have been found to be particularly useful. They allow high separation performance with low pressure drops. As reaction column, it is advantageous to use a rectification column having from 5 to 100, preferably from 20 to 50, actual or theoretical plates.

The bottom of the reaction column is heated by at least one built-in and/or external heater. The external heater can work with forced circulation or natural convection.

The operating pressure of the reaction column is advantageously from 0.5 to 7 bar, preferably from 1 to 5 bar and particularly preferably from 1 to 3 bar (absolute). The temperature at the bottom depends on the nature of the first carboxylic ester and/or first alcohol and in the reaction of methyl formate with ethanol is usually from 50 to 150° C., preferably from 60 to 100° C.

The reaction can be carried out in the presence of a suitable catalyst, e.g. an acidic or basic catalyst, preferably a basic catalyst. The catalyst can be either a heterogeneous catalyst or a homogeneously soluble catalyst. For the purposes of the present patent application, "homogeneously soluble" means that the catalyst used is soluble to an extent of more than 1 g/100 ml at 22° C. in at least the first alcohol used.

Heterogeneous basic catalysts are advantageously fixed in place in the reaction zone. Heterogeneous catalysts are, for example, selected from among basic oxides, mixed oxides or hydroxides and ion exchangers in amine or hydroxyl form.

The materials can be shaped as such or embedded in an oxidic binder matrix, e.g. of aluminum oxides, silicon dioxide, mixtures of finely divided silicon dioxide and aluminum oxide, titanium dioxide, zirconium dioxide or clay, to give shaped bodies such as extrudates or pellets. The heterogeneous basic catalyst is preferably present in particulate form having a particle size (maximum dimension) of from 1 to 10 mm, preferably from 1 to 4 mm.

Anion exchangers in hydroxyl form, e.g. styrene and acrylic resins having quaternary ammonium groups bound to an insoluble styrene or acrylic polymer matrix, are likewise suitable.

The heterogeneous catalyst is introduced into the reaction zone in such a way that sufficient interstices remain for mass transfer by rectification to be able to take place. The catalyst is preferably used in a concentration of 10-60% by volume, based on the empty volume of the column.

The heterogeneous catalyst can be accommodated on trays or be installed as catalyst bed in the reaction zone. However, it is also possible to use catalyst-comprising packings such as Montz MULTIPAK or Sulzer KATAPAK or introduce the catalyst in the form of random packing elements into the column. It is also possible to introduce the heterogeneous catalyst between an inert woven or knitted fabric, e.g. of fiberglass, and roll it up into bales. The bales can be arranged next to and above one another in such a way that the bales of one layer cover the interstices of the layer underneath. Furthermore, catalyst-filled woven mesh bags (known as Texas Tea Bags) can be used.

As an alternative, the heterogeneous catalyst has a particle size and shape which enable it to be introduced as packing, optionally in admixture with inert packing elements, into the reaction zone.

Homogeneously soluble basic catalysts are, if used, introduced into the reaction column at any suitable point in the lower to middle column region, advantageously together with the first alcohol.

The homogeneously soluble catalysts used are, for example, selected from among alkali metal hydroxides and/or alkoxides, e.g. potassium methoxide, sodium methoxide. The catalysts are advantageously introduced in the form of a solution in a suitable solvent. A preferred solvent is the first or second alcohol used in the process of the invention.

The homogeneously soluble catalyst is, if used, usually employed in an amount of from 0.00001 to 0.2 equivalent, preferably from 0.0001 to 0.1 equivalent and in particular from 0.0005 to 0.05 equivalent, based on the first carboxylic ester.

The first feed stream is preferably introduced laterally into the reaction column at least one first feed point between top and bottom of the reaction column and the second feed stream is introduced laterally into the reaction column at a second feed point located above the first feed point. The reaction zone extends at least partly into the column section between the first and second feed points.

The second feed stream is preferably introduced into the reaction column in the middle column region, i.e. preferably at the level of a plate which divides the number of plates of the column above it to the plates underneath it in a ratio of from 3:1 to 1:3, preferably from 2:1 to 1:2.

In general, from 0.5 to 2 equivalents, preferably from 0.7 to 1.2 equivalents and in particular from 0.9 to 1.1 equivalents, of first alcohol, based on the first carboxylic ester, are introduced into the system.

The continual removal of the reaction products from the reaction zone is achieved by the mass transfer processes occurring in the reaction column. Vapors of a low-boiling fraction comprising the second carboxylic ester formed and unreacted first carboxylic ester and also entrained unreacted first alcohol and second alcohol leave the reaction zone. The low-boiling fraction goes into an enrichment section of the reaction column in which the entrained unreacted first alcohol and the second alcohol are separated off and run back into the reaction zone.

A product fraction comprising the second carboxylic ester and unreacted first carboxylic ester can be taken off at an offtake located above the second feed point, preferably as a side offtake stream.

In many cases, the second carboxylic ester and the first carboxylic ester form an azeotrope with the alcohols, so that the composition of the product fraction corresponds essentially to the azeotropic composition. The product fraction can comprise minor amounts of first alcohol and second alcohol.

At the top of the reaction column, mainly unreacted first carboxylic ester is condensed and partly returned as overhead runback to the reaction column and partly taken off as overhead fraction. In a preferred embodiment, the overhead fraction is at least partly returned to the reaction zone, for example by mixing into the first feed stream. A further part of the overhead fraction can be discharged in order to prevent accumulation of low boilers.

In addition, a condensate of a high-boiling fraction comprising unreacted first alcohol and second alcohol together with entrained second carboxylic ester and unreacted first carboxylic ester runs down from the reaction zone. The high-boiling fraction goes into a stripping section of the column in which the entrained second carboxylic ester and unreacted first carboxylic ester are stripped out and recirculated to the reaction zone.

At the bottom of the reaction column, a bottom fraction comprising the second alcohol and unreacted first alcohol can be taken off. To discharge high boilers formed, part of the bottom fraction can be discarded.

The bottom fraction is preferably separated by distillation into second alcohol and unreacted first alcohol, preferably in a further distillation column. It is advantageous to recirculate at least part of the unreacted first alcohol to the reaction zone, for example by mixing it into the second feed stream.

The product fraction generally comprises not only the second carboxylic ester but also unreacted first carboxylic ester and small amounts of second alcohol and unreacted first alcohol. The product fraction is therefore preferably separated by distillation into pure second carboxylic ester and a fraction comprising unreacted first carboxylic ester. The separation by distillation is preferably carried out continuously in a second column. Preference is given to recirculating at least part of the fraction comprising the unreacted first carboxylic ester to the reaction zone, for example by mixing into the first feed stream.

The product fraction usually comprises azeotropes of the second carboxylic ester with second alcohol and unreacted first alcohol and also unreacted first carboxylic ester. Since the azeotropic composition is generally pressure-dependent, the azeotrope is separated by distillation at a pressure which is different from the pressure in the reaction column. This phenomenon is known as dual pressure process or pressure swing rectification or pressure swing distillation to those skilled in the art. At a pressure which is different from the pressure in the reaction column, the composition of the product fraction corresponds to a different azeotropic composition. In the second column, the second carboxylic ester can be taken off in pure form at the bottom or in the lower part of the column, e.g. close to the bottom region of the column, while an azeotropic mixture is obtained at the top, albeit with a significantly different composition than that of the product fraction. This azeotropic mixture can be fed back into the reaction zone.

The pressure which is different from the pressure in the reaction column can be, for example, from 1 to 40 bar, preferably from 5 to 15 bar (absolute).

In a preferred embodiment of the process in which the first carboxylic ester is methyl formate and the first alcohol is ethanol, the stream obtained at the bottom of the second column comprises from 99.0 to 100% by weight (in particular from 99.8 to 100% by weight) of ethyl formate, from 0 to 1% by weight (in particular from 0 to 0.2% by weight) of ethanol and from 0 to 1% by weight (in particular from 0 to 0.2% by weight) of other compounds.

As an alternative, the separation by distillation of the product fraction can be carried out as an extractive distillation.

The invention is illustrated by the accompanying drawing and the following examples.

FIG. 1 schematically shows a plant suitable for carrying out the process of the invention.

A first alcohol is introduced into the reaction column T1 via a side inlet 2 located at the upper end of the reaction zone 1. A heterogeneous catalyst (not shown) is fixed in place in the reaction zone. A first carboxylic ester is introduced into the reaction column T1 via a side inlet 3 located at the lower end of the reaction zone 1. The reaction to give the second carboxylic ester and the second alcohol takes place in the reaction zone 1. The second carboxylic ester and unreacted first carboxylic ester go into the enrichment section 4 of the reaction column T1 where they are largely freed of entrained second alcohol and unreacted first alcohol. A product fraction comprising the second carboxylic ester and unreacted first carboxylic ester is taken off via the side offtake 6. Second alcohol and unreacted first alcohol from the reaction zone 1 go into the stripping section 5 of the reaction column T1 where they are stripped of entrained second carboxylic ester and unreacted first carboxylic ester. The bottom fraction taken off via line 7 comprises mainly second alcohol and unreacted first alcohol.

The vapor 8 obtained at the top of the reaction column is condensed and partly returned via line 9 as overhead runback to the reaction column and partly conveyed as feed to the reaction zone via line 10.

The product fraction taken off from the reaction column T1 at the side offtake 6 is fed to a distillation column T2 in its upper region. The column T2 is operated at a different pressure, in general a higher pressure, than the reaction column T1. Pure second carboxylic ester is obtained at the bottom of the distillation column T2 and is discharged via line 11. The stream taken off at the top of the distillation column T2 is recirculated via line 12 to the reaction column T1.

The bottom fraction from the reaction column T1 is taken off via line 7 and fed to a distillation column T3. There, it is separated into second alcohol, which is taken off at the top of the column T3 via line 13, and first alcohol, which is obtained at the bottom of the column T3 and is recirculated via line 14 to the reaction column T1.

Example

Simulation

About 60 g/h of ethanol are fed at plate 10 into a reaction column which has 30 theoretical plates and is operated at 1 bar. At plate 5, 81 g/h of methyl formate is fed in. It is assumed that the reaction to form ethyl formate and methanol occurs to the chemical equilibrium at the plates located in between.

The reflux ratio of the reaction column is about 11. The overhead condensate, which consists essentially of methyl formate, is partly returned as runback and partly recirculated to the lower part of the reaction column.

At a side offtake at plate 25, 305 g/h of a mixture comprising about 60.0% by weight of ethyl formate, 27% by weight of methyl formate, 6% by weight of methanol and 2% by weight of ethanol is taken off.

This mixture is fed in at the top of a distillation column having 30 theoretical plates at a pressure of 7 bar. At the bottom of this distillation column, 100 g/h of a mixture comprising about 99.9% by weight of ethyl formate and 0.1% by weight of ethanol was obtained. The overhead distillate is partly returned as runback (reflux ratio about 3) and partly recirculated to the reaction column.

At the bottom of the reaction column, about 242 g/h of a mixture comprising about 19% by weight of methanol and 81% by weight of ethanol is taken off. This mixture is fractionated in a further distillation column having 30 theoretical plates at a pressure of 1 bar. Methanol is taken off at the top; the about 99% strength by weight ethanol obtained at the bottom is recirculated to the reaction column.

The invention claimed is:

1. A process for preparing a carboxylic ester by transesterification, the process comprising:
   introducing a first feed stream comprising a first carboxylic ester and a second feed stream comprising a first alcohol into a reaction column;
   reacting the first carboxylic ester with the first alcohol in a reaction zone of the reaction column to form a second carboxylic ester and a second alcohol; and
   continually removing the second carboxylic ester and the second alcohol from the reaction zone,
   wherein:
   the first alcohol has a higher molecular weight than the second alcohol;
   the first feed stream is introduced laterally into the reaction column at at least one first feed point located between the top and the bottom of the reaction column; and
   the second feed stream is introduced laterally into the reaction column at a second feed point located above the first feed point, wherein: a product fraction comprising the second carboxylic ester and unreacted first carboxylic ester is removed at an offtake point located above the second feed point; and a bottom fraction comprising the second alcohol and unreacted first alcohol is removed at the bottom of the reaction column.

2. The process according to claim 1, wherein an overhead fraction consisting essentially of the unreacted first carboxylic ester is additionally removed the top of the reaction column.

3. The process according to claim 2, wherein the overhead fraction is at least partly recirculated to the reaction zone.

4. The process according to claim 1, further comprising:
   distilling the product fraction to separate the second carboxylic ester and a fraction comprising the unreacted first carboxylic ester; and at least partly recirculating the fraction comprising the unreacted first carboxylic ester to the reaction zone.

5. The process according to claim 4, wherein the distilling of the product fraction occurs at a pressure which is different than a pressure in the reaction column.

6. The process according to claim 4, wherein the distilling of the product fraction occurs as an extractive distillation.

7. The process according to claim 1, further comprising:
distilling the bottom fraction to separate the second alcohol and the unreacted first alcohol; and
at least partly recirculating the unreacted first alcohol to the reaction zone.

8. The process according to claim 1, wherein a soluble basic catalyst is introduced into the reaction column.

9. The process according to claim 1, wherein a heterogeneous basic catalyst is located in the reaction zone.

10. The process according to claim 1, wherein the first carboxylic ester is a formic ester.

11. The process according to claim 1, wherein the first alcohol is ethanol and the second alcohol is methanol.

12. The process according to claim 1, wherein:
the first carboxylic ester is methyl formate;
the first alcohol is ethanol; and
the second carboxylic ester is ethyl formate.

13. The process of claim 1, wherein the reaction column comprises a reaction zone, an enrichment section, and a stripping section.

14. The process of claim 1, wherein the second feed point is located in a medium column region at a level of a plate which divides the number of plates of the reaction column above it to the plates underneath it in a ratio of from 3:1 to 1:3.

15. The process of claim 5, wherein a pressure difference between a pressure of the reaction column and a pressure of the distilling of the product fraction is from 1 to 40 bar.

16. The process of claim 12, wherein the process yields a stream comprising from 99.0 to 100.0% by weight of the ethyl formate.

* * * * *